(12) United States Patent
Cantor

(10) Patent No.: US 10,869,979 B2
(45) Date of Patent: Dec. 22, 2020

(54) SUPRAGLOTTIC AIRWAY DEVICE

(71) Applicant: Eric A. Cantor, Stoughton, MA (US)

(72) Inventor: Eric A. Cantor, Stoughton, MA (US)

(*) Notice: Subject to any disclaimer, the term of this patent is extended or adjusted under 35 U.S.C. 154(b) by 215 days.

(21) Appl. No.: 16/100,006

(22) Filed: Aug. 9, 2018

(65) Prior Publication Data

US 2019/0076608 A1    Mar. 14, 2019

Related U.S. Application Data

(60) Provisional application No. 62/542,869, filed on Aug. 9, 2017.

(51) Int. Cl.
| | | |
|---|---|---|
| *A61M 16/10* | (2006.01) | |
| *A61M 16/04* | (2006.01) | |
| *A61M 16/08* | (2006.01) | |
| *A61M 39/06* | (2006.01) | |
| *A61M 16/06* | (2006.01) | |

(52) U.S. Cl.
CPC .... *A61M 16/0409* (2014.02); *A61M 16/0445* (2014.02); *A61M 16/0463* (2013.01); *A61M 16/0816* (2013.01); *A61M 16/0833* (2014.02); *A61M 16/0858* (2014.02); *A61M 16/105* (2013.01); *A61M 39/06* (2013.01); *A61M 16/0434* (2013.01); *A61M 16/0683* (2013.01); *A61M 16/1055* (2013.01); *A61M 2205/583* (2013.01)

(58) Field of Classification Search
None
See application file for complete search history.

(56) References Cited

U.S. PATENT DOCUMENTS

| | | | | |
|---|---|---|---|---|
| 5,957,134 A | * | 9/1999 | Lee | A61M 16/04 128/207.14 |
| 7,021,313 B1 | * | 4/2006 | Crump | A61M 16/0463 128/207.14 |
| 7,263,997 B2 | * | 9/2007 | Madsen | A61M 16/0463 128/207.14 |
| 7,556,041 B2 | * | 7/2009 | Madsen | A61M 16/0463 128/207.14 |
| 2008/0029100 A1 | * | 2/2008 | Glassenberg | A61B 1/04 128/207.15 |
| 2008/0142003 A1 | * | 6/2008 | Depel | A61M 16/0429 128/200.24 |

* cited by examiner

*Primary Examiner* — Bradley H Philips
*Assistant Examiner* — Savannah L Gabriel
(74) *Attorney, Agent, or Firm* — Adler Pollock & Sheehan P.C.

(57) ABSTRACT

A method and apparatus for a medical airway passage device suitable for maintaining an airway for a patient is provided. The medical airway passage device includes a novel coupler device designed to prevent contamination, infection, and unwanted discharge of patient fluids and solids during usage. The coupler includes a locking mechanism configured to lock the coupler to a breathing tube and thus preventing unintentional decoupling of the coupler from the breathing tube. The coupler also includes a self-sealing suction port for removing patient discharges. The coupler further includes a filter for enabling the free flowing passage of airflow but prevention of the flow of patient discharges.

15 Claims, 10 Drawing Sheets

SUPRAGLOTTIC AIRWAY DEVICE

FIELD OF THE INVENTION

The present invention relates to a medical airway device such as an endotracheal tube, a tracheal tube, or catheter medical device suitable for maintaining an airway for a patient. In particular, the present invention relates to a supraglottic airway device configured to reduce potential contamination exposure to a patient and exposure to patient discharge to a medical professional.

BACKGROUND

Generally, medical airway devices, such as endotracheal tubes, are designed to be inserted through the mouth or nose of a patient to establish and maintain an airway for a patient to enable sufficient exchange of oxygen and carbon dioxide. Types of endotracheal tubes include oral or nasal, cuffed or un-cuffed, pre-formed (e.g. RAE (Ring, Adair, and Elwyn) tube), reinforced tubes, and double-lumen endobronchial tubes. Conventional endotracheal tubes can be modified to include an inflatable cuff to seal the trachea and bronchial tree against air leakage and aspiration of gastric contents, blood, secretions, and other fluids. Conversely, endotracheal tubes can be un-cuffed, but un-cuffed endotracheal tubes are often limited to usage with pediatric patients. Another type of endotracheal tube is the double-lumen endo-bronchial tube, which is utilized for ventilating each lung independently for specific applications (e.g., thoracic surgery). Another common modification to an endotracheal tube includes a small second lumen opening above the inflatable cuff, which is typically used for suctioning of secretions which sit above the cuff which helps reduce the risk of chest infections in long-term intubated patients.

However, these conventional endotracheal tube devices, and other similarly designed airway devices, have a number of shortcomings. In particular, conventional endotracheal tubes typically include one breathing tube with an unsecured or inadequately secured coupler device, a lack of a means to perform suction effectively, and provide no filter to prevent bodily fluids/secretions from propelling from the airway and out the endotracheal tube. The unsecured or inadequately secured coupler device can fall off due to a combination of factors including loose connection to the breathing tube, condensation created in the breathing tube during use that causes a friction fit to give way and slide, patient secretions, secured too tightly to a bag valve mask, etc. If the coupler device unintentionally falls off of the breathing tube, it is problematic because the coupler device should remain sterile to prevent contamination, infection, etc. to the patient, and after falling onto the ground it no longer is sterile. Additionally, when the coupler device is intentionally removed (e.g., to perform deep tracheal suctioning) the same risks are present as when the coupler device unintentionally falls off of the breathing tube. Additionally, removal of the coupler device, intentional or unintentional, also leaves an open orifice at the proximal end of the tube to the patient, which allows for excess patient discharges to flow out.

Although removing the coupler device to perform suctioning is undesirable, continuous subglottic suctioning and frequent intermittent subglottic suctioning drainage of subglottic secretions, via a cuffed endotracheal tube, are associated with up to a 50% decrease in the incidence of gastric aspiration, a potential cause of ventilator-associated pneumonia (VAP). Therefore, with conventional medical airway devices, it is sometimes necessary to intentionally remove the coupler.

SUMMARY

There is a need for improvements to conventional medical airway device designs, such as endotracheal tube designs. The present invention is directed to further solutions to address this need, in addition to having other desirable characteristics. Specifically, an improved supraglottic airway device is provided to reduce unintentional removal of the coupler device while providing improved suctioning and filtering of patient discharges through the device.

In accordance with example embodiments of the present invention, a supraglottic airway device is provided. The device includes an elongate breathing tube having a first open end and a second open end, and a removable and replaceable male-to-male coupler disposed within the first open end in a locked-in position. The coupler includes a first cylindrical male end adapted to couple with the breathing tube with an interference fit between a tube-engaging side surface of the coupler and an inner wall of the breathing tube and a second cylindrical male end opposite the first. The coupler also includes a first detent disposed on the tube-engaging side surface of the first cylindrical male end and a port within the coupler itself disposed in and passing through the tube-engaging side of the first cylindrical male end. The device also includes a first recess disposed in the inner wall of the breathing tube, sized, dimensioned, and positioned in such a way that the first recess engages with the first detent of the coupler when the coupler is in the locked-in position within the first open end of the breathing tube.

In accordance with aspects of the present invention, the device comprises an endotracheal tube or other supraglottic airway devices. The device can further include a self-closing seal disposed in a self-closable suction port. The device can further include a contaminant blocking air pass filter disposed within the first cylindrical male end of the coupler. The second cylindrical male end can be sized, dimensioned, and configured for engagement with a ventilator or a bag-valve mask.

In accordance with aspects of the present invention, the device can further include an inflatable cuff disposed proximal the second open end of the breathing tube. The device can further include one or more radio-opaque line demarcations disposed on the breathing tube. The device can further include a second detent disposed on the tube-engaging side surface of the first cylindrical male end. The device can further include a second recess disposed in the inner wall of the breathing tube, sized, dimensioned, and positioned to engage with the first detent of the coupler when the coupler is disposed within the first open end of the breathing tube in such a way that removably locks the coupler with the breathing tube. The device can further include an opening disposed in and passing through the breathing tube. The opening can be disposed in and passing through the breathing tube comprises a suction port adapted to receive a suction tube. The breathing tube, or the coupler device in itself, also comprises a pressure port for trained medical providers' specific use.

In accordance with example embodiments of the present invention, a method for operating a supraglottic airway device is provided. The method includes inserting a first male end, which may be cylindrical, of a removable and replaceable male-to-male coupler into a first open end of an elongate breathing tube forming an interference fit between a tube-engaging side surface of the coupler and an inner wall of the breathing tube. The method also includes aligning a first detent disposed on the tube-engaging side surface of the first male end of the coupler with a first recess disposed in the inner wall of the breathing tube, sized, dimensioned, and positioned in such a way that the first recess engages with the first detent of the coupler.

BRIEF DESCRIPTION OF THE FIGURES

These and other characteristics of the present invention will be more fully understood by reference to the following detailed description in conjunction with the attached drawings, in which.

DETAILED DESCRIPTION

An illustrative embodiment of the present invention relates to a medical airway passage device suitable for maintaining an airway for a patient. The medical airway passage, or supraglottic airway, device includes a novel coupler device designed to prevent undesired or unintentional un-coupling, contamination, infection, and unwanted discharge of patient fluids and solids during usage. The coupler includes a locking mechanism configured to lock the coupler to a breathing tube, and thus, prevent undesired or unintentional un-coupling of the coupler from the breathing tube. The locking mechanism includes one or more detents configured to form an interference fit between the coupler device and a breathing tube. The interference fit prevents the coupler device from unintentionally becoming dislodged from the breathing tube during use.

The coupler also includes a side port including a self-closing seal configured to receive a suction device for removing patient discharges from the breathing tube and/or coupler. The side port is configured such that the coupler does not need to be removed from the breathing tube to perform the suction operation. The coupler further includes a filter for enabling the free flowing passage of airflow while preventing the flow of patient fluid discharges.

Figure 1:
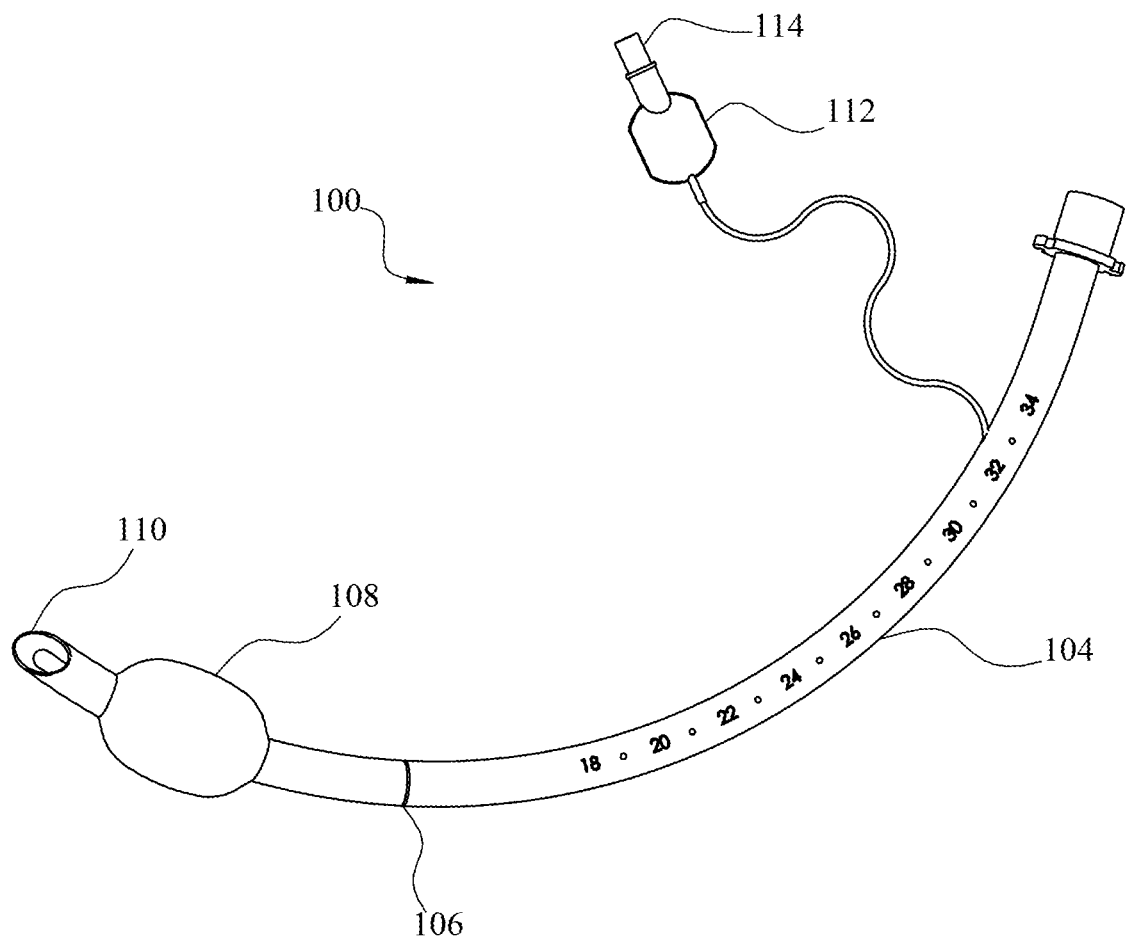
FIG. 1 is an illustrative example of a conventional endotracheal tube system known in the art.

FIG. 1 depicts an example illustration of a conventional endotracheal tube 100. The conventional endotracheal tube 100 includes a connector or coupler device 102, a breathing tube 104, a vocal cord level indicator 106 and other demarcations, a cuff 108, a beveled opening 110, a pilot balloon 112, and a self-sealing valve 114. As depicted in FIG. 1, the coupler device 102 is attached to one end of the breathing tube 104. Traditionally, the coupler 102 is coupled to the breathing tube 104 via a friction fit by inserting the coupler 102 into the open end of the breathing tube 104. At the opposing end of the breathing tube 104 is the beveled opening 110. Additionally, the cuff 108 and vocal cord level indicator 106 located proximal to the beveled opening 110. The cuff 108 is an inflatable element which is inflated to form a seal against a tracheal wall of a patient. The seal created by an inflated cuff 108 prevents gases from leaking past the cuff 108 and allows positive pressure ventilation.

As would be appreciated by one skilled in the art, not all conventional endotracheal tube 100 designs include each of the elements provided in FIG. 1. For example, a conventional endotracheal tube 100 can be an un-cuffed design and not include the cuff 108. The conventional endotracheal tube 100 can also include the pilot balloon 112 and self-sealing valve 114 located proximal to a mid-section of the conventional endotracheal tube 100, as depicted in FIG. 1. The pilot balloon 112 is connected to the cuff 108 by a thin tube.

Figure 2:
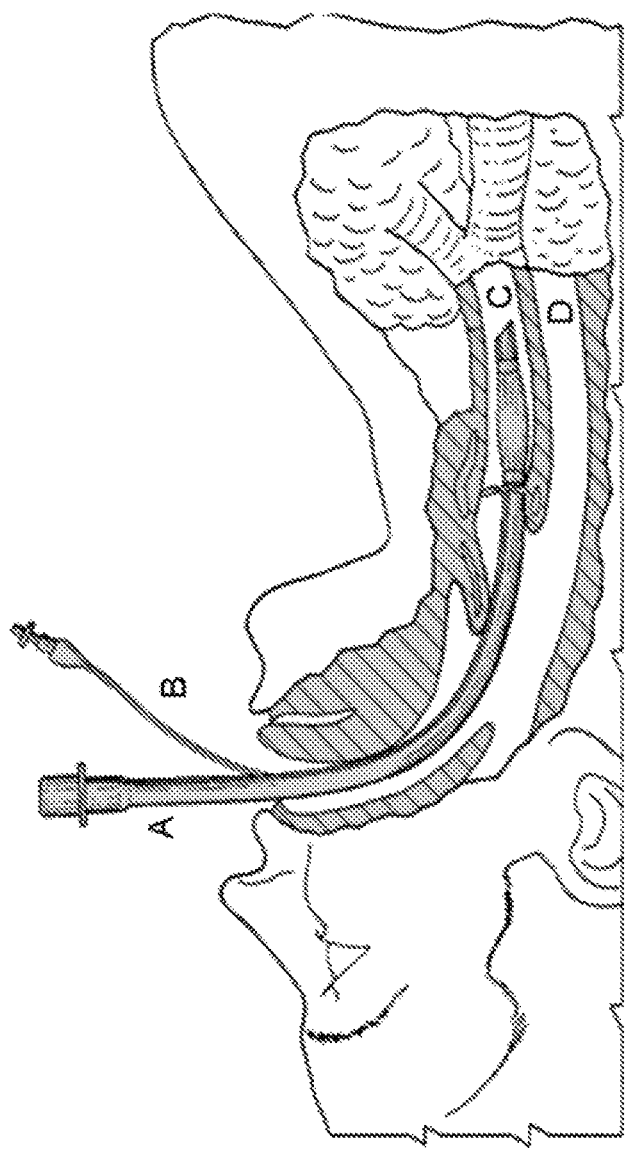
FIG. 2 is a diagrammatic illustration of utilization of a conventional endotracheal tube known in the art.

In practice, the conventional endotracheal tube 100 can be inserted into the trachea 202 of a patient 200, starting with the beveled end 110, to assist the patient in exchanging oxygen and carbon dioxide, as depicted in FIG. 2. When the conventional endotracheal tube 100 is inserted in the trachea 202 of the patient 200, the coupler device 102, the pilot balloon 112, and the self-sealing valve 114 are located outside of the patient 200 for access by a medical professional. A syringe can be inserted into the self-sealing valve 114 and as the syringe supplies pressurized air, the pilot balloon 112 and cuff inflate 108. Once the cuff 108 is inflated the syringe is removed. Air does not leak out as there is a one way valve at the pilot balloon 112. Additionally, when feeling the pilot balloon 112, a medical professional can estimate an amount of pressure in the cuff 108. For example, if the cuff 108 is leaking, the pilot balloon 112 will collapse.

FIGS. 3 through 5H, wherein like parts are designated by like reference numerals throughout, illustrate a first example embodiment of an improved medical airway device or supraglottic airway device, particularly an endotracheal tube device, according to the present invention. Although the present invention will be described with reference to the example embodiment or embodiments illustrated in the figures, it should be understood that many alternative forms can embody the present invention. One of skill in the art will additionally appreciate different ways to alter the parameters of the embodiment(s) disclosed, such as the size, shape, or type of elements or materials, in a manner still in keeping with the spirit and scope of the present invention.

Figure 3:
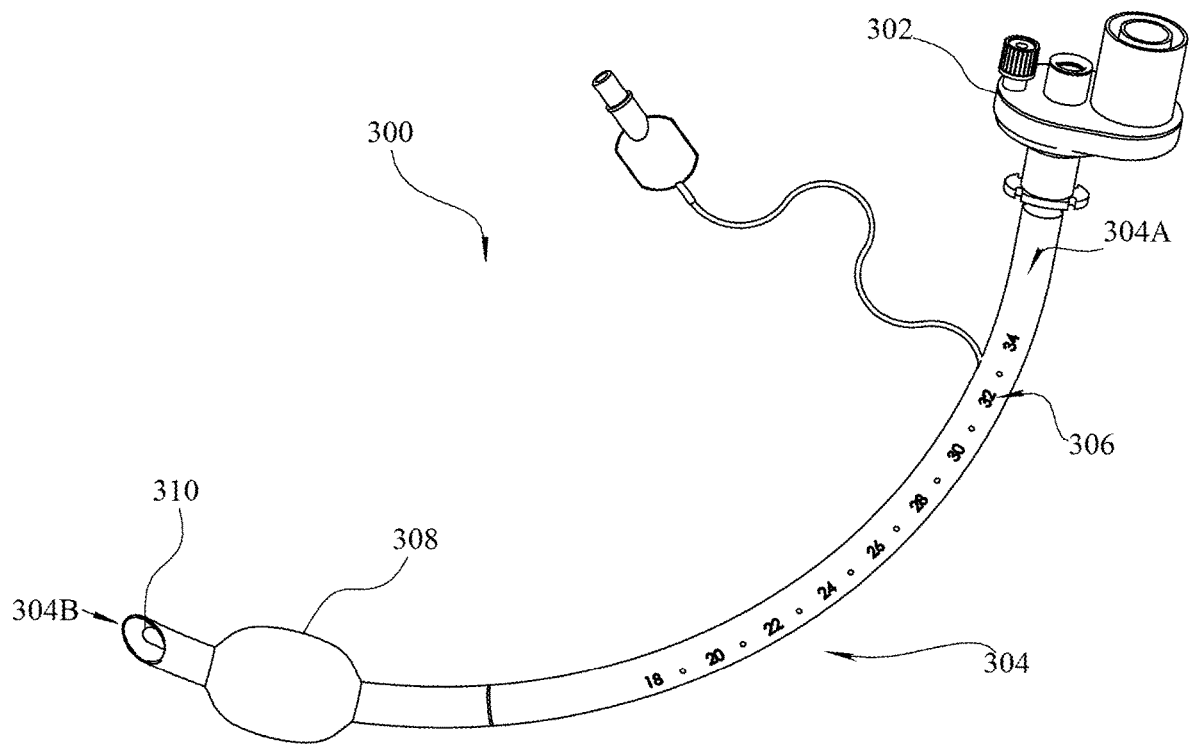
FIG. 3 is an illustrative example of a supraglottic airway device, in accordance with aspects of the invention.

FIG. 3 depicts a supraglottic airway device in accordance with the present invention. In particular, FIG. 3 depicts an endotracheal tube device 300 embodiment, including an elongate breathing tube 304 having a first open end 304a and a second open end 304b. The endotracheal tube device 300 also includes a removable and replaceable coupler 302 disposed at and coupled to the first open end 304a of the breathing tube 304. The replaceable coupler 302 of the present invention includes a combination of novel elements not found in traditional couplers (e.g., coupler 102) for airway devices, as discussed in greater detail with respect to FIGS. 4-5H. The device 300 may also include a breathing valve 400 to enable introduction of air to the patient, and a pressure relief port 500 to enable relief of buildup content in the breathing tube 304. The pressure relief port 500 may be used to removably engage a pressure application apparatus as needed.

The endotracheal tube device 300, as depicted in FIG. 3, also includes other traditional elements of a conventional endotracheal tube 100. For example, the endotracheal tube device 300 includes a vocal cord level indicator 306 and other traditional line demarcations disposed on the breathing tube 304, an inflatable cuff 308 (disposed proximal the second open end of the breathing tube), a beveled opening 310 located at the second end 304b of the breathing tube 304, a pilot balloon 312, and a self-sealing valve 314. As would be appreciated by one skilled in the art, the endotracheal tube device 300 of the present invention can alternatively not include a cuff 308 and related elements without departing from the scope of the present invention. The breathing tube 304, the cuff 308, the beveled opening 310 located at the second end 304b of the breathing tube 304, the pilot balloon 112 corresponding to that of FIG. 1, and the self-sealing valve 114 corresponding to that of FIG. 2, of the endotracheal tube device 300 share the same functionality known in the art and as discussed with respect to FIGS. 1 and 2. As would be appreciated by one skilled in the art, the novel elements of the present invention are not intended to be limited to an endotracheal tube but can be implemented for use with any applicable medical airway device known in the art. For example, the present invention can be adapted for use as any combination of airway devices utilizing a breathing tube 304 and a coupler 302 including but not limited to a supraglottic airway device or a supraglottic airway device; such as: The King, Combi-tube, LMA and any other non-invasive (blind-insertion) tubes utilized to protect/ventilate the airway of a patient. Additionally, all sizes of medical airway devices will be accounted for, and implementations will be incorporated on all adult sizes with the possibility of implementation to infant/child size breathing tubes.

Figure 4A:
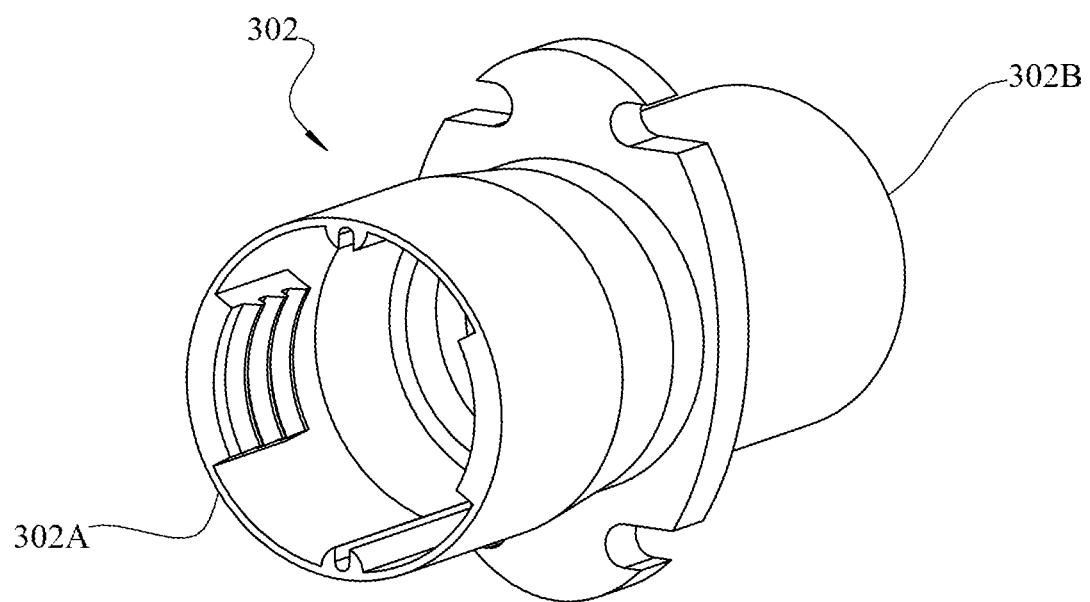
FIG. 4A is a bottom perspective view showing the inside of the device.
Figure 4B:
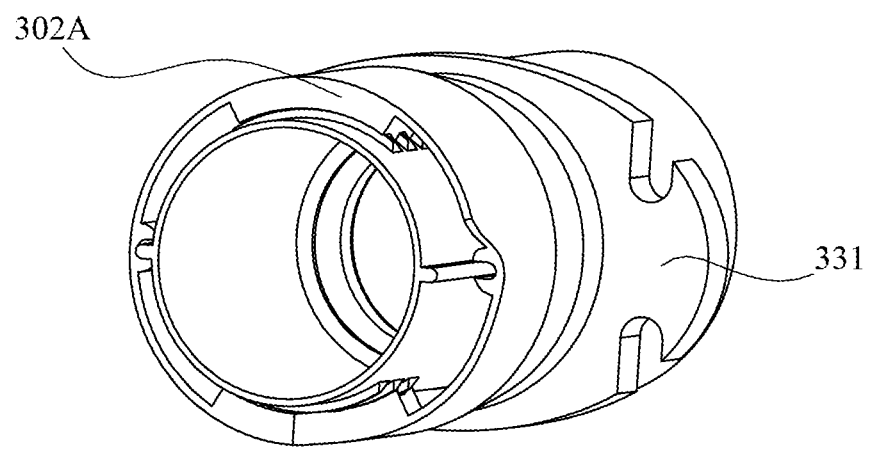
FIG. 4B is a top perspective view showing the inside of the device.
Figure 4C:
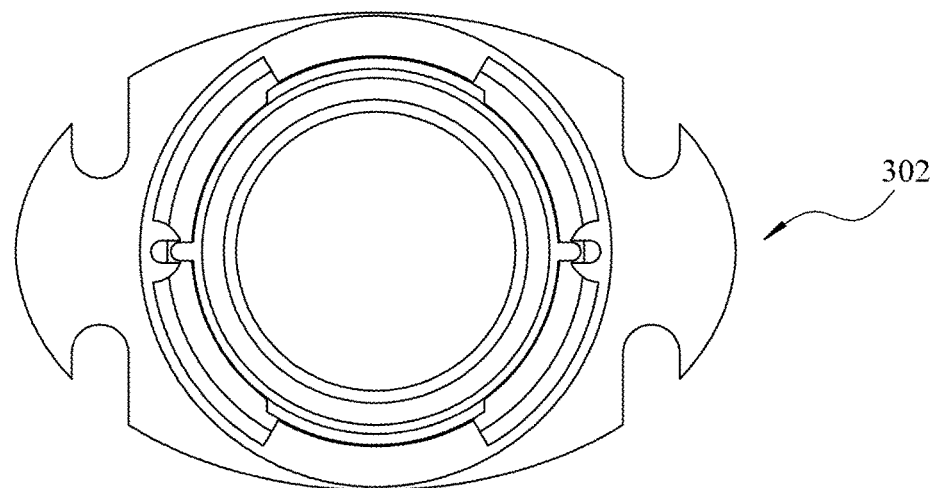
FIG. 4C is a partial cutaway side view of a first embodiment of the coupler device for use with an endotracheal tube, in accordance with aspects of the invention.
Figure 4D:
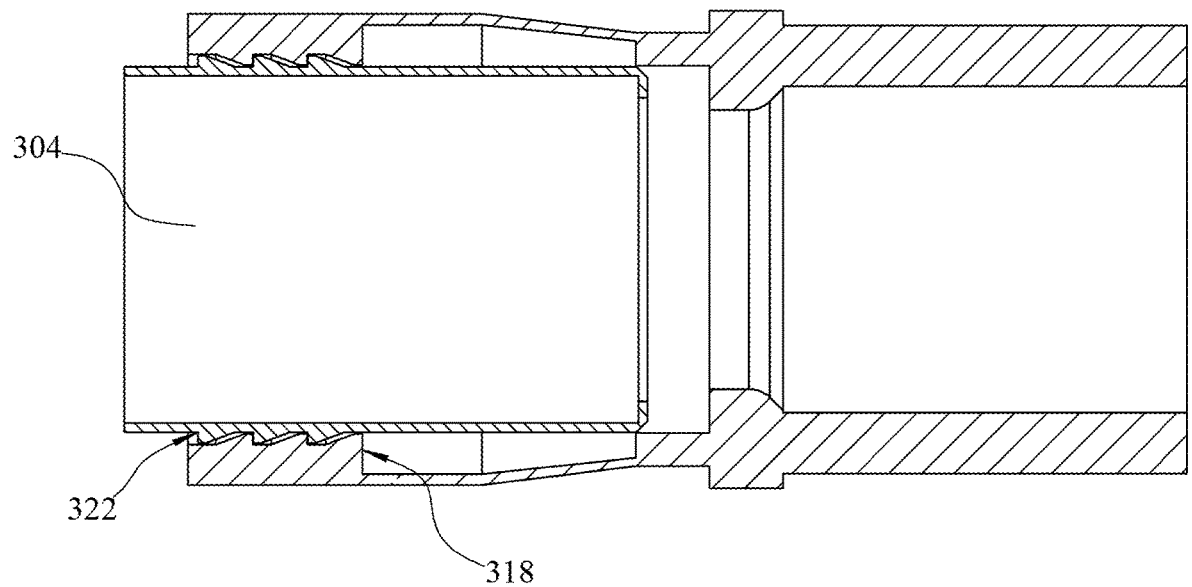
FIG. 4D is a bottom perspective view of the device.

FIGS. 4A-4D depict example illustrations of the coupler 302 of the present invention. In particular, FIG. 4A depicts a representative illustration of the coupler 302 and FIG. 4B depicts an exploded view of the coupler 302. FIG. 4C depicts a two-dimensional/flattened view of the coupler 302, and FIG. 4D depicts the locking mechanics of the coupler 302 to the tube 304. In accordance with an example embodiment of the present invention, the coupler 302 is a male-to-male coupler, as depicted in FIGS. 4A-4D. More specifically, the coupler 302 includes a first cylindrical male end 302a and a second cylindrical male end 302b opposite the first cylindrical male end 302a. The first cylindrical male end 302a is adapted to couple (in a locked-in position) with a breathing tube 304 when positioned within the first open end 304a of the breathing tube 304. In particular, the first cylindrical male end 302a is configured in a locked-in position with the breathing tube 304 via an interference fit created between a tube-engaging side surface 318 of the coupler 302 and an inner wall of the breathing tube 304. A ring component 331 to enable attachment of the tube 304 to the patient provides a smooth engagement mechanism for doing so for trained medical provider usage.

In accordance with an example embodiment of the present invention, the interference fit is further enhanced by use of a first detent 322 disposed on the tube-engaging side surface 318 of the first cylindrical male end 302a engaging with a recess 304a disposed in the inner wall of the breathing tube 304. In particular, the detent 322 on the tube-engaging side surface 318 of the first cylindrical male end 302a engages with a first recess disposed in the inner wall of the breathing tube 304, which is sized, dimensioned, and positioned in such a way that the first recess engages with the first detent of the coupler 302. The first recess is not shown in the figure but it would be readily understood by those of skill in the art that the recess would be a notch, groove, or the like that engages with the detent 322. Additionally, the first recess can be a singular location, multiple locations, or can be in the form of a ring shaped groove around an entire circumference of the breathing tube 304. When the detent 322 of the coupler 302 is disposed within the indent of the breathing tube 304, the coupler 302 is in the locked-in position within the first open end 304a of the breathing tube 304 by engaging with the first recess.

Figure 5A:
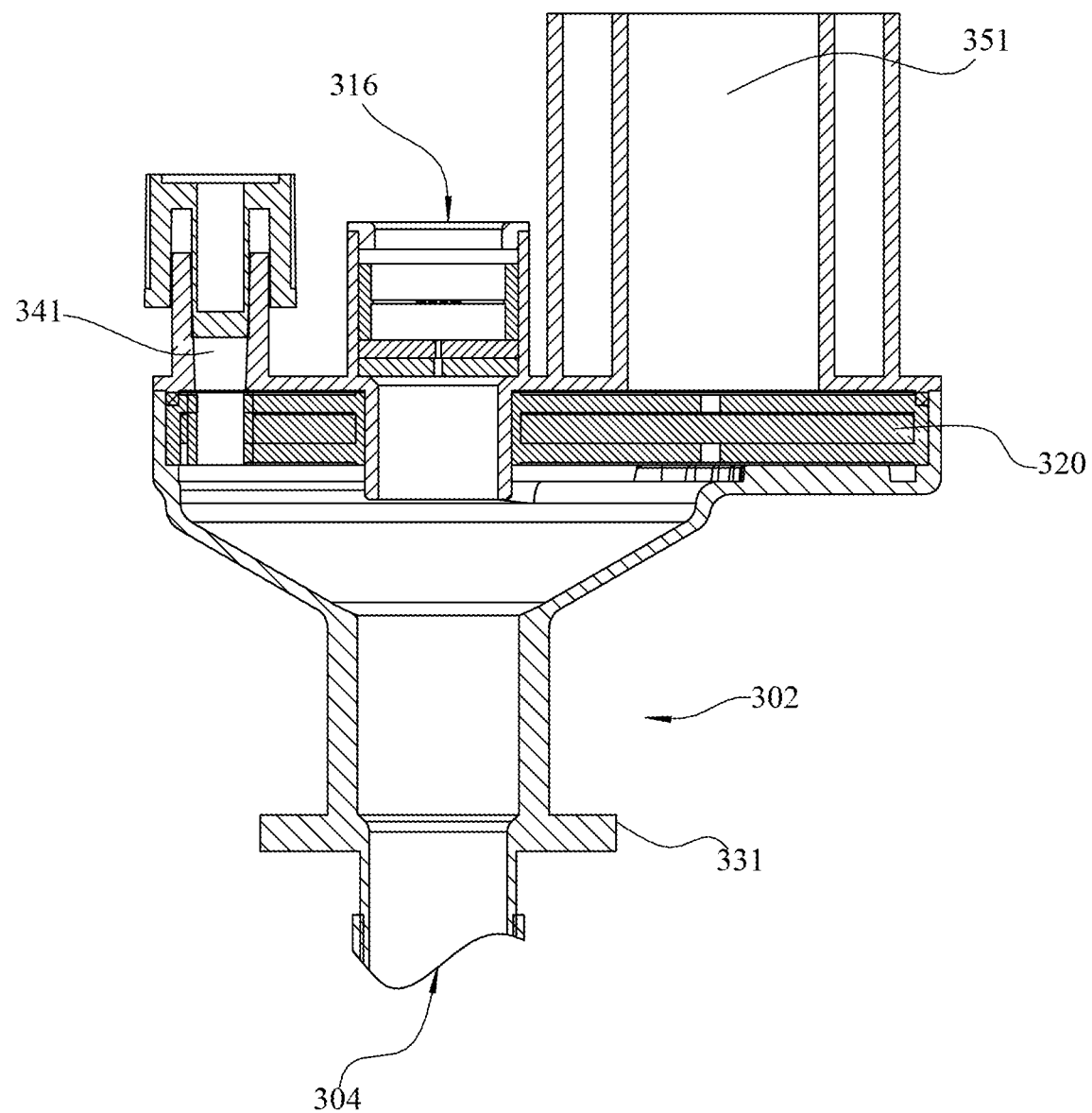
FIGS. 5A-5H illustrate components of the coupler device of FIG. 4, in accordance with aspects of the invention.

In accordance with an example embodiment of the present invention, the interference fit is established by the relative size of the coupler 302 to the breathing tube 304. As shown in FIG. 5A, for example, the breathing tube 304 stretches to fit over the coupler 302, thereby creating a tight interference fit between the tube-engaging side surface 318 of the coupler 302 and the inner wall of the breathing tube 304. One of skill in the art would appreciate the specific dimensions of the coupler 302 must be sized to engage with the specific dimensioned breathing tube in any instance to create the described stretching of the breathing tube 304 and resulting interference fit. As would be appreciated by one skilled in the art, the coupler 302 can include any number of detents 322 (and corresponding indentations or holes) configured to engage with the breathing tube 304. For example, the coupler 302 can include a second detent disposed on the tube-engaging side surface 318 of the first cylindrical male end 302a of the coupler 302. The combination of the one or more detents 322 with the recess 304a and the interference fit of the coupler 302 with the inner wall of the breathing tube 304, create a substantially improved removable coupling between the breathing tube 304 and the coupler 302, which prevents the undesired or unintentional un-coupling of the breathing tube 304 from the coupler 302 that is evident in the prior conventional devices. The coupler device 302 includes a housing that contains the self-closable suction port 316, a pressure port 341 and a ventilation port 351. FIGS. 5B-5H depict different angles and components, as well as interior and exterior views of the device as shown in FIG. 5A.

In accordance with an example embodiment of the present invention, the coupler 302 is removably but securely coupled with the breathing tube 304 as described above. Alternatively, the coupler 302 can be fixedly or permanently attached to the breathing tube 304 through any combination of non-toxic glues, heat sealing, mold manufacturing process, etc. The fixedly attached implementation of the coupler 302 and the breathing tube 304 would form a single piece airway device.

In accordance with an example embodiment of the present invention, a closable suction port 316 is disposed in and passing through the tube-engaging side 318 of the first cylindrical male end 302a of the coupler 302, as depicted in FIGS. 3-6. In accordance with this example embodiment, the breathing tube 304 will include a hole at a location lining up with the suction port 316 of the coupler 302 when the coupler 302 is locked into place. In other words, there is a hole disposed in and passing through the breathing tube 304 and having a central axis in alignment with a central axis of the suction port 316 of the coupler 302 when the coupler 302 is in the locked-in position. The hole in the breathing tube 304 will enable liquid discharged from the patient to pass from the breathing tube 304 through the self-closable suction port 316 in the coupler 302 (e.g., via a suction device).

In an alternative embodiment, the coupler 302 includes the self-closable suction port 316 disposed in and passing through the tube as depicted in FIGS. 4A and 4C. Regardless of the placement of the suction port 316, the opening in the breathing tube 304 and the opening of the suction port 316 are intended to align and match up substantially in shape and substantially in dimension.

Regardless of placement, the suction port 316 includes a self-closing seal 316a disposed in the suction port 316. The self-closing seal 316a of the suction port 316 can be closed to prevent discharge (e.g., mucous, blood, vomit, other bodily fluids, etc.) from the patient from exiting the endotracheal tube device 300 or the suction port 316 can be opened such that a suction device can be inserted therein to remove solid and fluid discharge from the patient. Additionally, the suction port 316 is configured such that a suctioning tube (not depicted) can be left in place connected to the coupler 302 (and breathing tube 304) without having to risk another sterile piece of equipment becoming unsterile by the same means the coupler 302 can become contaminated (e.g., unintentional removal). This feature allows the medical provider to always know where the suction tubing is, and have the capability of turning on/off suction immediately, when needed. As would be appreciated by one skilled in the art, any self-closing design known in the art for the seal can be utilized for the suction port 316, depending on the desired opening and closing of the self-closing seal 316a of the suction port 316. For example, a gasket with pie shaped slits can be utilized as the self-closing seal 316a of the suction port 316, as depicted in FIG. 4D.

In accordance with an example embodiment of the present invention, the second cylindrical male end 302b is sized, dimensioned, and configured for coupling with traditional medical devices in a similar fashion as traditional couplers (e.g., coupler 102). For example, the second cylindrical male end 302b of the coupler 302 is configured for engagement with a ventilator, a bag-valve mask, a catheter mount, etc., as would be readily appreciated by those of skill in the art.

Figure 5B:
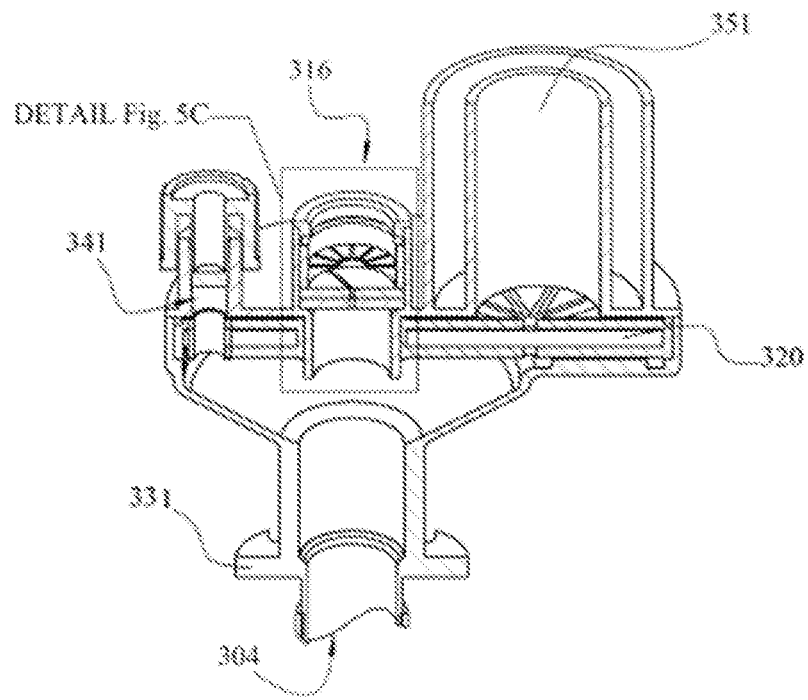
Figure 5C:
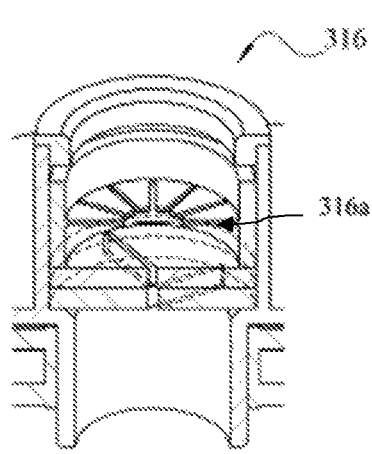
Figure 5D:
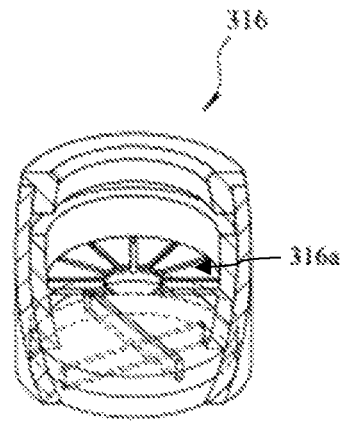
Figure 5E:
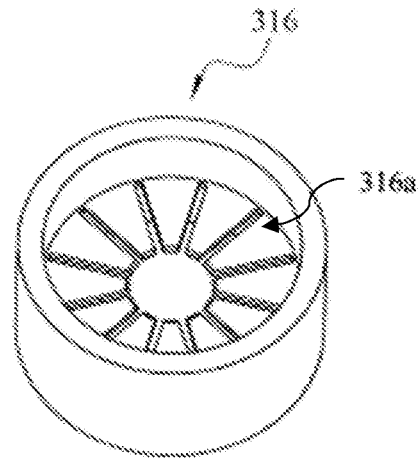
Figure 5F:
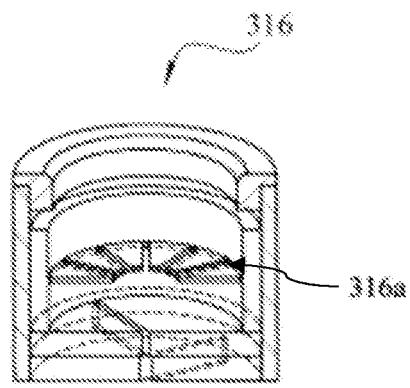
Figure 5G:
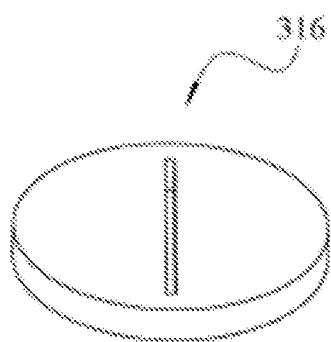
Figure 5H:
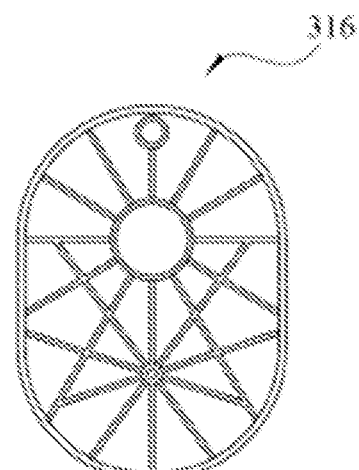

FIG. 5B depicts a close up view of the coupler 302 disposed at and coupled to the first open end 304a of the breathing tube 304 to result in the endotracheal tube device 300 of the present invention. In particular, FIG. 5B depicts the coupler 302 removably locked into place with the breathing tube 304 (e.g., via the detent 322 and the interference fit of the tube-engaging side surface 318 of the coupler 302 engaged with the inner wall of the breathing tube 304) and the suction port 316 including the self-closing seal 316a is provided through the side of coupler 302 and the breathing tube 304.

Continuing with FIGS. 4A-4D, in accordance with an example embodiment of the present invention, the coupler 302 further includes a contaminant blocking air pass filter 320 disposed therein. In particular, the filter 320 allows air to flow freely there through, but minimizes or inhibits liquid/solid content diffusion through the filter 320 and through the second cylindrical male end 302b of the coupler 302. Therefore, the filter 320 will allow air to enter and exit the breathing tube 304 while preventing secretions/fluids from exiting through the second cylindrical male end 302b of the coupler 302. As would be appreciated by one skilled in the art, the filter 320 can include any material known in the art to perform such filtering. In accordance with an example embodiment of the present invention, as depicted in FIGS. 3-5H, the filter 320 is disposed within the second cylindrical male end 302b of the coupler 302 after the suction port 316.

Figure 6A:
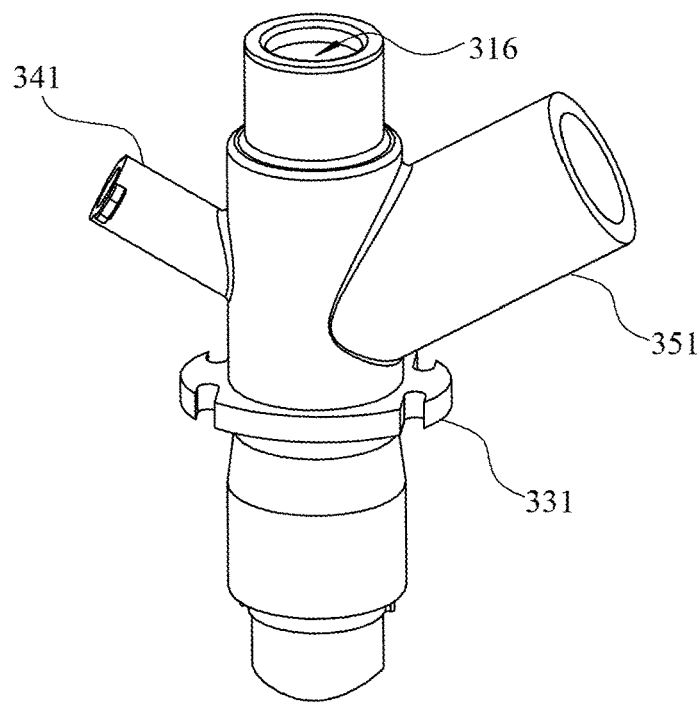
FIG. 6A is a side view of a second embodiment of the coupler device, in accordance with aspects of the present invention.
Figure 6B:
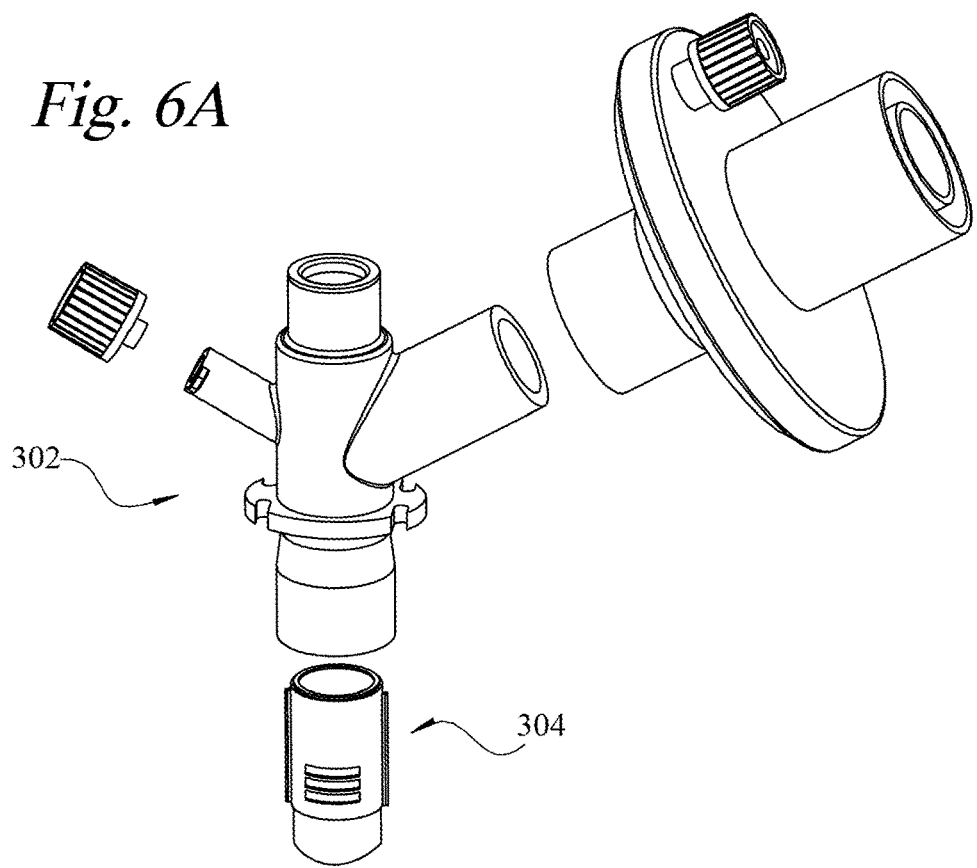
FIG. 6B is an exploded side view of the coupler device of FIG. 6A and showing a breathing valve attachment.

In an alternative embodiment of the present invention, the filter 320 is disposed within the first cylindrical male end 302a of the coupler 302 prior to the suction port 316, as depicted in FIGS. 6A and 6B. Regardless of the placement of the suction port 316 within the coupler 302, which primary purpose is provided for suction of materials from the tube, the suction port 316 will always be placed before the filter 320. FIGS. 6A and 6B further depict an alternative ergonomic embodiment of the coupler 302 where the ventilation port 351 is angled/beveled so as not to interfere with the anterior area of the patient (not having the BVM or ventilator tubing resting on the patient's face). The device of FIGS. 6A and 6B optionally also includes the pressure relief port 500.

In operation, the design and elements of the coupler 302 are configured to reduce exposure of patient discharges, expelled forcefully and non-forcefully from a breathing tube 304, to a medical professional while utilizing an airway breathing apparatus (such as an endotracheal tube device 300). The reduction of such exposure is provided through the combination of improvements to the coupler 302. In particular, the tube-engaging side surface 318 of the coupler 302 securely locks the coupler 302 in place at the end of the breathing tube 304 using a combination of an interference fit and a detent engaging with a recess as described herein. The locking mechanism provided by the tube-engaging side surface 318 of the coupler 302 also prevents the coupler 302 from decoupling from the breathing tube 304 and contaminating the coupler 302 and/or the breathing tube 304. As would be appreciated by one skilled in the art, the coupler 302 and the breathing tube 304 should remain sterile to ensure the best medical care to the patient while reducing risks of infection and other issues. The best way to keep the coupler 302 and breathing tube 304 sterile is to maintain the coupling between the two pieces.

Additionally, the inclusion of the suction port 316 enables improved suction operation (e.g., via a suction device of tube inserted into the endotracheal tube device 300) such that the coupler 302 does not need to be intentionally removed for such operations. In other words, although the coupler 302 can optionally be de-coupled from the breathing tube 304, the present invention eliminates any such reason to because of the self-closing seal 316a disposed within the suction port 316 of the coupler 302 (and optionally through the breathing tube 304). The self-closing seal 316a allows suction tubing (e.g., French catheter tubing) to be inserted into the suction port 316 without having to remove the coupler 302 from the breathing tube 304. As would be appreciated by one skilled in the art, any removal of the coupler 302 intentional (e.g., suction) or otherwise increases the chances of the coupler 302 and the breathing tube 304 becoming unsterile and/or lost.

In addition, the inclusion of the filter 320 of the coupler 302 prevents low and high concentrations of patient discharges to expel directly out of the endotracheal tube device 300 or other airway device. In particular, the filter 302 provides the medical provider with an extra barrier of cross-contamination/exposure which is common in the field. By reducing a volume of discharges, the filter 302 reduces tension experienced by a medical professional when ventilating a patient which can reduce forceful ventilation and hyperventilation, which can harm the patient. Additionally, the filter 302 provides a passive benefit by restricting the medical provider's (bag squeeze) to overly/forcefully ventilate the patient with a bag valve mask. Moreover, the filter 302 will produce a semi-trap so all the content of the discharges contained within the coupler 302 and breathing tube 304 can be suctioned out with ease (e.g., via the suction port 316). As would be appreciated by one skilled in the art, discharges in and around the breathing tubes that re-enter the patient's anatomy increases chance of infections, pneumonia, etc. As would be appreciated by one skilled in the art, the coupler 302 can include each of the elements 316, 318, 320 or some combination of those features.

Overall, the features of the present invention are designed to increase positive outcomes in cardiac/respiratory arrest patients and patients that are in need of advanced airways by reducing infection overall. The patient benefits from the features of the present invention, and the medical provider assisting the patient's airway has a lower risk of exposure from patient contents. These benefits are achieved through the reduction in chances of pieces of the airway device losing sterility, a reduction of aspiration and ventilation pneumonia, easy-access suctioning, prevention of medical provider exposure to bodily fluids, and a reduction in hyperventilation.

Figure 7:
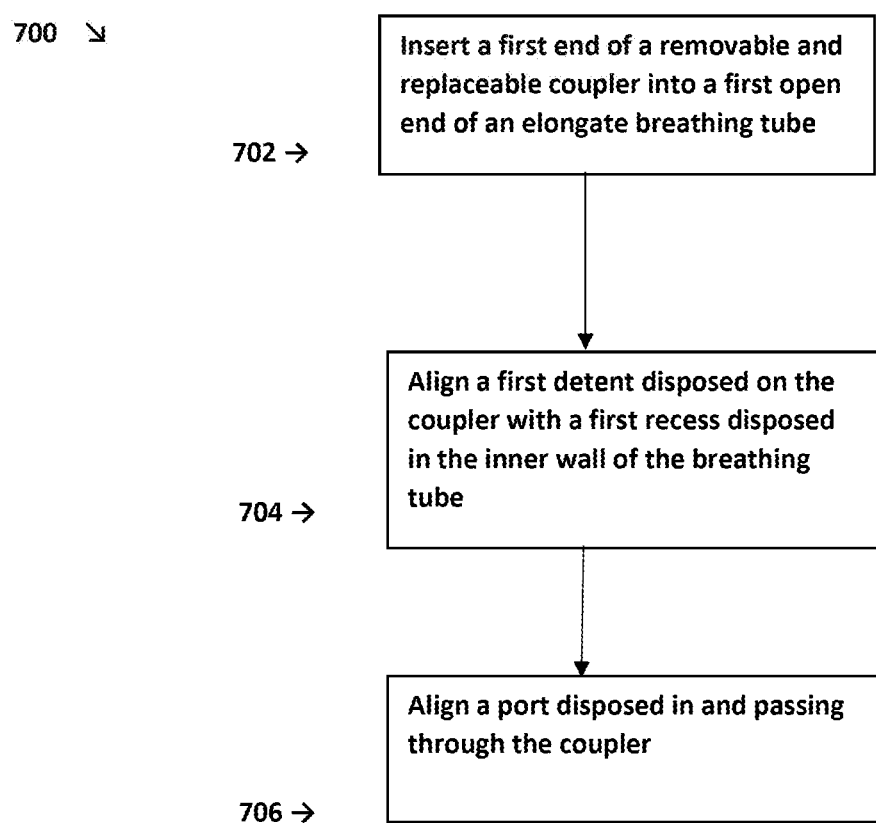
FIG. 7 is an illustrative flow chart depicting utilization an endotracheal tube, in accordance with aspects of the invention.

FIG. 7 depicts a method 700 for operating a supraglottic airway device. At step 702 a user inserts a first cylindrical male end of a removable and replaceable male-to-male coupler into a first open end of an elongate breathing tube forming an interference fit between a tube-engaging side surface of the coupler and an inner wall of the breathing tube. At step 704 the user aligns a first detent disposed on the tube-engaging side surface of the first cylindrical male end of the coupler with a first recess disposed in the inner wall of the breathing tube, sized, dimensioned, and positioned in such a way that the first recess engages with the first detent of the coupler. At step 706 the user aligns a side port disposed in and passing through the tube-engaging side of the first cylindrical male end. Upon completion of steps 702-706 of the method 700 the supraglottic airway device is ready for utilization on a patient.

As utilized herein, the terms "comprises" and "comprising" are intended to be construed as being inclusive, not exclusive. As utilized herein, the terms "exemplary", "example", and "illustrative", are intended to mean "serving as an example, instance, or illustration" and should not be construed as indicating, or not indicating, a preferred or advantageous configuration relative to other configurations. As utilized herein, the terms "about", "generally", and "approximately" are intended to cover variations that may exist in the upper and lower limits of the ranges of subjective or objective values, such as variations in properties, parameters, sizes, and dimensions. In one non-limiting example, the terms "about", "generally", and "approximately" mean at, or plus 10 percent or less, or minus 10 percent or less. In one non-limiting example, the terms "about", "generally", and "approximately" mean sufficiently close to be deemed by one of skill in the art in the relevant field to be included. As utilized herein, the term "substantially" refers to the complete or nearly complete extend or degree of an action, characteristic, property, state, structure, item, or result, as would be appreciated by one of skill in the art. For example, an object that is "substantially" circular would mean that the object is either completely a circle to mathematically determinable limits, or nearly a circle as would be recognized or understood by one of skill in the art. The exact allowable degree of deviation from absolute completeness may in some instances depend on the specific context. However, in general, the nearness of completion will be so as to have the same overall result as if absolute and total completion were achieved or obtained. The use of "substantially" is equally applicable when utilized in a negative connotation to refer to the complete or near complete lack of an action, characteristic, property, state, structure, item, or result, as would be appreciated by one of skill in the art.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. A supraglottic airway device, comprising:
an elongate breathing tube having an outer wall and an inner wall, and including
a first open end,
a second open end opposite the first end and having a beveled opening,
a longitudinal hole disposed in and passing through the elongate breathing tube, and having a first central axis, and
a vocal cord level indicator disposed along the outer wall of the elongate breathing tube;
an inflatable cuff disposed proximal the second open end;
a pilot balloon operably attached to the elongate breathing tube;
a self-sealing valve proximate the pilot balloon; and
a coupler assembly including
a first cylindrical male end having
a tube-engaging side surface configured to insertably engage the first open end of the elongate breathing tube so as to form an interference fit with the inner wall of the elongate breathing tube, the tube-engaging side surface including at least one detent for non-threadably engaging the inner wall in the interference fit, and
a ring component configured to enable attachment of the elongate breathing tube to a patient,
a second cylindrical male end configured for coupling with a medical device, and having a contaminant-blocking air pass filter, and
a housing having
a suction port disposed in and passing through the tube-engaging side surface of the first cylindrical male end, the suction port having a second central axis that is alignable with the first central axis of the longitudinal hole of the elongate breathing tube and a self-closing seal having a gasket with pie-shaped slits therein,
a pressure port, and
a ventilation port wherein a distal-most edge of the second cylindrical male end is wider than a proximal-most edge of the first cylindrical male end, and the contaminant-blocking air pass filter extends across an entirety of the second cylindrical male end without covering the suction port and optionally without covering the pressure port.

2. The device of claim 1, wherein the second cylindrical male end is sized, dimensioned, and configured for engagement with a ventilator or a bag-valve mask.

3. The device of claim 1, wherein the pressure port is disposed near the suction port.

4. The device of claim 1, wherein the vocal cord level indicator includes one or more radio-opaque line demarcations disposed on the breathing tube.

5. The device of claim 1, wherein the at least one detent of the tube-engaging side surface of the first cylindrical male end includes two detents.

6. The device of claim 1, the suction port is adapted to receive a suction tube.

7. The device of claim 1, wherein the ventilation port is disposed near the suction port.

8. A supraglottic airway device, comprising:
an elongate breathing tube having an outer wall and an inner wall, and including a first open end and a second open end opposite the first end;
an inflatable cuff disposed proximal the second open end;
a pilot balloon operably attached to the elongate breathing tube;
a self-sealing valve proximate the pilot balloon; and
a coupler assembly including
a first cylindrical male end having
a tube-engaging side surface configured to insertably engage the first open end of the elongate breathing tube so as to form an interference fit with the inner wall of the elongate breathing tube, the tube-engaging side surface including at least one detent for non-threadably engaging the inner wall in the interference fit,
a second cylindrical male end configured for coupling with a medical device, and having a contaminant-blocking air pass filter, and
a housing having
a suction port disposed in and passing through the tube-engaging side surface of the first cylindrical male end, and a self-closing seal,
a pressure port, and
a ventilation port wherein a distal-most edge of the second cylindrical male end is wider than a proximal-most edge of the first cylindrical male end, and the contaminant-blocking air pass filter extends across an entirety of the second cylindrical male end without covering the suction port and optionally without covering the pressure port.

9. The device of claim 8, wherein the first cylindrical male end further includes a ring component configured to enable attachment of the elongate breathing tube to a patient.

10. The device of claim 8, wherein the self-closing seal includes a gasket with pie-shaped slits therein.

11. The device of claim 8, wherein the suction port is adapted to receive a suction tube.

12. The device of claim 8, wherein the at least one detent of the tube-engaging side surface of the first cylindrical male end includes two detents.

13. The device of claim 8, wherein the second cylindrical male end is configured for engagement with a ventilator.

14. The device of claim 8, wherein the second cylindrical male end is configured for engagement with a bag-valve mask.

15. The device of claim 8, wherein the second cylindrical male end is configured for engagement with a catheter mount.

* * * * *